United States Patent [19]
Chen

[11] Patent Number: 5,963,429
[45] Date of Patent: Oct. 5, 1999

[54] PRINTED CIRCUIT SUBSTRATE WITH CAVITIES FOR ENCAPSULATING INTEGRATED CIRCUITS

[75] Inventor: Philip H. Chen, Angleton, Tex.

[73] Assignee: Sulzer Intermedics Inc., Angleton, Tex.

[21] Appl. No.: 08/915,437

[22] Filed: Aug. 20, 1997

[51] Int. Cl.⁶ .............................. H01L 23/31; H05K 1/18
[52] U.S. Cl. .................... 361/764; 361/761; 361/783; 257/686; 257/723; 257/777; 257/787; 438/126; 600/374
[58] Field of Search ..................... 361/761, 763, 361/764, 783, 820; 257/686, 723, 724, 777, 778, 787, 920; 438/107–110, 126, 127; 439/909; 600/374; 607/4

[56] References Cited

U.S. PATENT DOCUMENTS

| | | | |
|---|---|---|---|
| 5,182,632 | 1/1993 | Bechtel et al. | 257/724 |
| 5,373,843 | 12/1994 | Quedens et al. | 439/909 |
| 5,608,262 | 3/1997 | Degani et al. | 257/723 |
| 5,646,828 | 7/1997 | Degani et al. | 361/761 |
| 5,801,438 | 9/1998 | Shirakawa et al. | 257/686 |
| 5,831,833 | 11/1998 | Shirakawa et al. | 361/764 |

FOREIGN PATENT DOCUMENTS

| | | | |
|---|---|---|---|
| 59-44852 | 3/1984 | Japan | 257/724 |
| 2-26080 | 1/1990 | Japan | 257/724 |
| 6-21328 | 1/1994 | Japan | 257/777 |
| 7-030059 | 1/1995 | Japan . | |

OTHER PUBLICATIONS

Direct Chip Interconnect Using Polymer Bonding by Ken Gilleo, IEEE publ. no. 0569–5503/89/0037, pp. 37–39, 1989.

*Primary Examiner*—Leo P. Picard
*Assistant Examiner*—John B. Vigushin
*Attorney, Agent, or Firm*—Schwegman, Lundberg, Woessner & Kluth, P.A.

[57] ABSTRACT

A printed circuit board substrate includes cavities in which electronic components, such as integrated circuits, are mounted and encapsulated. Once the electronic components are encapsulated, other electronic components can be mounted above the encapsulated component on the top surface of the substrate, thereby increasing the number of components that can be mounted to a circuit board of a given area. The encapsulated components are mounted using any one of a variety of techniques. The substrate may include multiple conductive layers for electrically interconnecting the encapsulated components to other components.

8 Claims, 4 Drawing Sheets

PRINTED CIRCUIT SUBSTRATE WITH CAVITIES FOR ENCAPSULATING INTEGRATED CIRCUITS

BACKGROUND OF THE INVENTION

1. Field of the Invention

The present invention relates generally to printed circuit boards. More particularly, the invention relates to techniques for mounting integrated circuits and other electrical components on a substrate and electrically interconnecting the devices.

2. Description of the Related Art

Most electronics equipment manufactured today includes integrated circuits ("IC's") and other electrical components mounted on printed circuit boards ("PCB"). Printed circuit boards (alternatively called "printed wiring boards") allow the IC's to be interconnected in a cost effective and reliable manner.

Referring now to FIG. 1, a conventional PCB 20 is shown to include a substrate 21 and a number of IC's 24, 26, 28, 30, 32. It should be recognized that the substrate is shown disproportionately thick for ease of understanding. The substrate is constructed of plastic, ceramic, or other suitable material. Further, the substrate may include multiple layers of conductive sheets. In accordance with known manufacturing techniques, the conducting layers are sandwiched together, with each conductive layer separated by an insulating layer. Electrical connections between the components mounted on the top of the substrate are made via conductive "traces" on the top surface 22 of the PCB (an exemplary trace 27 is shown FIG. 1). Other connections are made by traces on one or more of the conductive layers included within the substrate.

Referring now to FIG. 2, two exemplary IC's 24, 26 are shown in a cross-sectional view bonded to the top surface 22 of substrate 21 using a conductive epoxy 25 or other conductive adhesive. Electrical connections between each IC 24, 26 and the substrate are made by way of wire bonds 34a, 34b, 34c, and 34d. Wire bonds 34a–34d electrically couple contacts 29 on the top surface of each IC to contacts 23a, 23b, 23c, and 23d (referred to as "pads" and also shown in FIG. 1) disposed on the top surface 22 of the substrate 21. The wire bonds 34 are thin, curved loops of wire, typically made of gold or aluminum.

Referring still to FIG. 2, IC 24 electrically couples to IC 26 by way of a trace on conductive layer 36. Pads 23b and 23c electrically connect to conductive layer 36 by way of conducting channels 38 and 40 included within substrate 21. Conducting channels 38, 40 couple to layer 36 at points 37 and 39, respectively. To prevent conducting channels 38, 40 from electrically coupling to other conducting layers between pads 23b, 23c and layer 36, conducting channels 38, 40 are contained within an insulated hole (not shown) in the substrate, commonly referred to as a "via" hole or simply "via." Thus, an electrical signal passing from IC 24 to IC 26 passes through wire bond 34b, pad 23b, conductive channel 38, layer 36 between points 37 and 39, conducting channel 40, pad 23c, and wire bond 34c.

Several disadvantages of current PCB technology are illustrated with respect to FIGS. 1 and 2. Referring to FIG. 1, a substrate has a limited surface area in which IC's and other electrical components can be mounted. Thus, there is a limit to the size and number of IC's that can be mounted on a given PCB. The number of IC's that are mounted on a given substrate is referred to as "packaging density." The size of a given substrate, and in particular its surface area, traditionally has placed an upper limit on packaging density.

For many types of electronic devices, the ability to provide a high packaging density is extremely important. Pacemakers and defibrillators, for example, include charging circuitry for charging capacitors to deliver electrical shocks to the heart, amplifier circuits for amplifying electrical signals produced by the heart, microprocessor circuitry for controlling operation of the device, as well as other components. It is now commonplace for pacemakers and defibrillators to be implanted inside the body. As implanted device technology has progressed, the requirements and capabilities of such devices have increased dramatically. Many of the technological advancements in implanted device technology have required the addition of new components to the device. Future advancement in implantable pacemaker and defibrillator technology may, and probably will, require still more electronic components to be included within the implanted device.

To minimize patient discomfort, it is desirable to make an implantable device as small as possible. Thus, implantable device manufacturers are faced with two conflicting design criteria. It is desired, on one hand, to include more components in the implantable device. At the same time, it is desirable to make the implantable devices even smaller so as to increase patient comfort. Moreover, being able to include more components in a smaller volume, i.e., increasing packaging density, has long been a design goal of all implantable device manufacturers. Likewise, for many other types of electronic equipment, such as laptop computers, digital watches, and hearing aids, increasing packaging density also is desirable.

Another disadvantage that must be endured with currently available printed circuit board designs is illustrated with reference to FIG. 2. As explained above, an electrical signal (i.e., electrical current) from IC 24 must pass through a length of conductive materials including wire bonds 34b and 34c, conducting channels 38 and 40 and layer 36 between points 37 and 39. It is known that an electrical conductor has a parameter referred to as resistance or more broadly, impedance. The impedance of a conductor is proportional to the length of the conductor—a longer conductor has a higher impedance than a shorter conductor for a given cross-sectional area. The impedance of a conductor causes a drop in voltage between opposite ends of the conductor as a result of the current that flows through the conductor. The resulting voltage drop increases as the length of the conductor increases. With reference to FIG. 2, a signal produced by IC 24 may have, for example, a voltage of 3 volts as the signal leaves IC 24 and enters wire bond 34b. However, because of the length of the conductor, comprised of wire bonds 34b and 34c, conducting channels 38 and 40 and layer 36, the voltage of the signal as it leaves wire bond 34c and enters IC 26 (the opposite end of the conductor) will be less than 3 volts. The magnitude of the voltage of the signal at IC 26 depends on the length of the conducting path through which the signal passes between IC 24 and IC 26. In some situations, as explained below, this voltage drop may be undesirable.

Referring again to the pacemaker and defibrillator example, IC 26 may be a capacitor, and IC 24 may be a charging circuit for charging the capacitor 26. The electrical charge stored in the capacitor 26 is used to deliver a shock to the heart according to known medical protocols. The charging circuit 24 generates and provides electrical charging current to the capacitor via wire bond 34b, conducting channel 38, layer 36, conducting channel 40, and wire bond 34c. The time it takes to charge a capacitor is a direct function of the efficiency of the charging process—a low efficiency charging process requires more time to charge a capacitor than a highly efficient charging process. The charging efficiency is less than 100% for the circuit of FIG. 2 because, among other reasons, electrical energy is lost as a result of the voltage drop along the conducting pathway between the charging circuit 24 and capacitor 26. Thus, it will take more time to charge capacitor 26 than if there was no voltage drop along the conducting pathway between charging circuit 24 and capacitor 26. Moreover, the length of the conducting pathway directly effects the charging time. For this reason and others, reducing the impedance of a conductive path often is desirable.

It would thus be desirable to have printed circuit board technology that allows for higher packaging density. Such a circuit board would allow for more electrical components to be included in a smaller volume than previously possible and thus would especially benefit those devices for which a smaller size is desirable. Further, printed circuit board technology that includes lower impedance conductive pathways also is desired. Despite the advancements made in printed circuit board technology, to date there is still room for improvement in these areas.

SUMMARY OF THE INVENTION

Accordingly, there is herein provided a printed circuit board that includes a substrate with cavities in which electronic components, such as integrated circuits, are mounted and encapsulated. The encapsulating material forms a portion of the top surface of the substrate. Once the electronic components are encapsulated, other electronic components can be mounted above the encapsulated component, thereby increasing the number of components that can be mounted to a circuit board of a given surface area. The substrate may include multiple conductive layers for electrically interconnecting the encapsulated components to other components.

The encapsulated components are mounted using any one of a variety of techniques. According to a first embodiment, the electronic component includes electrical contacts that are soldered directly to conductive pads on the bottom surface of the cavity. Alternatively, the contacts may be electrically coupled to the pads in the cavity by way of conductive tabs in a "flip tab" configuration. Further still, the cavity may include an upper portion and a lower portion, and the electronic component may be mounted in the bottom portion by either wire bonds or conductive tabs coupled to a surface between the upper and lower portions.

BRIEF DESCRIPTION OF THE DRAWINGS

Other objects and advantages of the invention will become apparent upon reading the following detailed description and upon reference to the accompany drawings, wherein.

DETAILED DESCRIPTION OF THE PREFERRED EMBODIMENT

Figure 3:
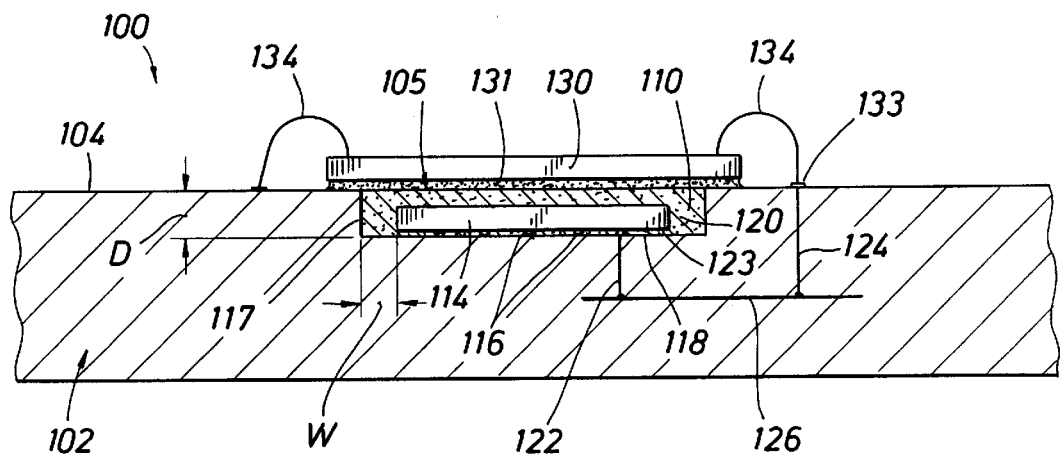
FIG. 3 is a cross-sectional view showing a cavity in a printed circuit board substrate for encapsulating an integrated circuit, in accordance with a preferred embodiment of the invention.

Referring now to FIG. 3, a multi-layer printed circuit board 100 includes a substrate 102, constructed in accordance with a preferred embodiment. Substrate 102 includes one or more cavities 110 in which an integrated circuit 114 is mounted. The cavities 110 are formed as cut-out portions in one or more of the layers comprising the multi-layer board 100. It should be recognized that the printed circuit board 100 in FIG. 3 is not drawn to scale, but rather is exaggerated for purposes of clarity. As will be explained in greater detail below, integrated circuit 114 is encapsulated in cavity 110 advantageously so as to allow other electrical components, such as integrated circuit 130, to be mounted to the top surface 104 of substrate 102, preferably over cavity 110.

Integrated circuit 114 is mounted in cavity 110 using any one of a number of mounting techniques. FIG. 3, for example, shows integrated circuit 114 mounted in a "flip chip" configuration. In a flip chip configuration, the IC is "flipped" over and electrically connected to the substrate via solder joints 116. The solder joints 116 thus provide an electrical connection between the electrical contacts on the top surface 123 of the inverted IC and substrate 102.

Once the IC 114 is mounted in cavity 110, the IC 114 is encapsulated with a "glob top" material 120, such as Hysol FP 4520 manufactured by Dexter, or any other suitable encapsulation material. The encapsulation material initially is a liquid and hardens as it sets. Once hardened, the encapsulation material 120 prevents IC 114 from becoming detached from substrate 102. Further, encapsulating the IC 114 in cavity 110 allows a surface 105 to form contiguous with top surface 104 of substrate 102. Surface 105 forms a "footprint" for the encapsulated IC. As such, another component, such as IC 130, can be mounted on footprint 105 over encapsulated IC 114 as shown in FIG. 3. The area of the surface-mounted component, such as IC 130, is also referred to as a footprint. As will be discussed in more detail below, the footprints of the encapsulated components and the components mounted to the top surface of the PCB may overlap only partially or completely. The IC 130 preferably mounts to substrate 102 using any one of a number of conventional mounting techniques, such as the use of an adhesive 131. Wire bonds 134, or other connection techniques may be used to provide electrical connections between the IC 130 and the surface 104 of substrate 102.

If desired, IC 114 can be electrically coupled to IC 130 by way of conductive layer 126. A conductive channel 122 couples IC 114 to layer 126 and another conductive channel 124 couples wire bond 134 to layer 126 via pad 133. Connections from IC 114 to other components on printed circuit board 100 are also possible by way of traces in one or more conductive layers in multi-layer printed circuit board 100.

Figure 4:
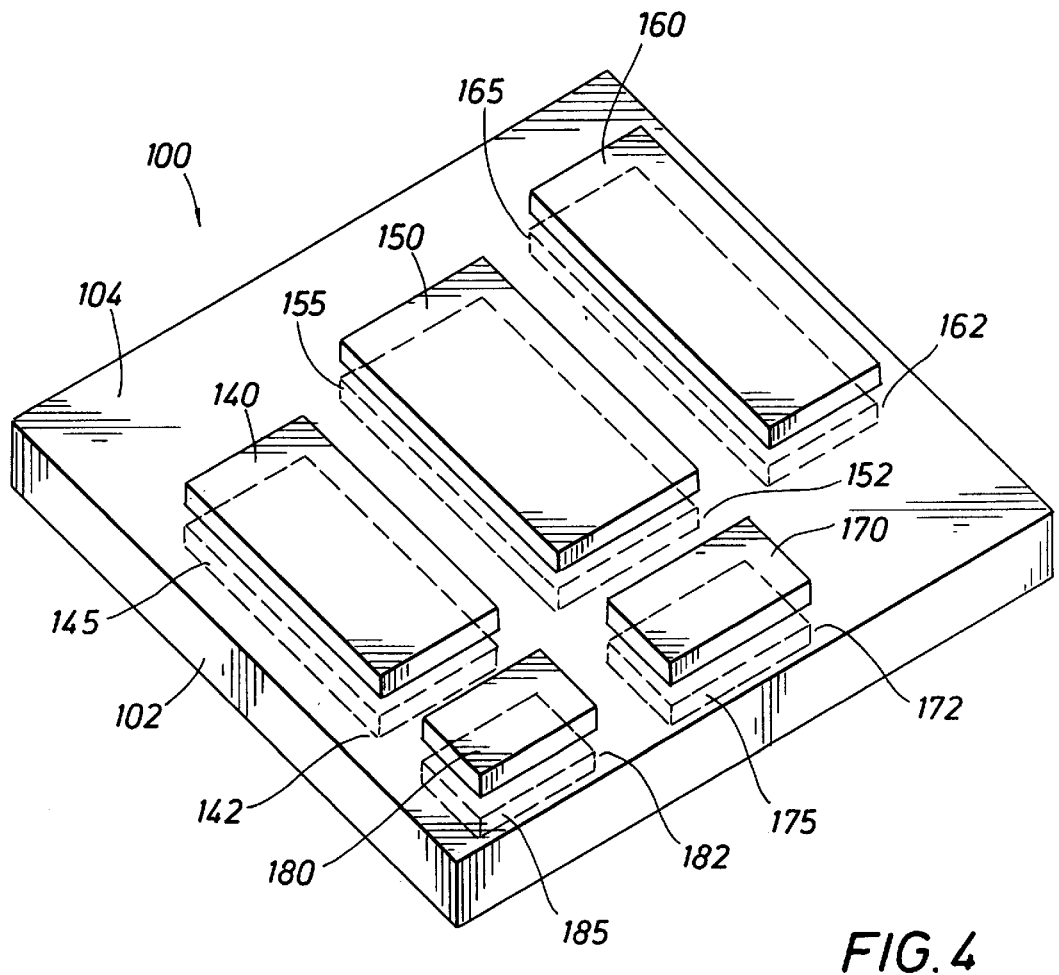
FIG. 4 is perspective view showing a printed circuit board with a plurality of integrated circuits encapsulated in cavities, in accordance with the preferred embodiment.

The preferred embodiment shown in FIG. 3 advantageously allows for an increase in packaging density as two electrical components (such as IC's 114, 130) can be mounted generally in the same portion of a circuit board, rather than requiring extra surface area for both components to be mounted on the outer surface of the circuit board as in previous PCB's. The increase in packaging density provided by the preferred embodiment is further illustrated in FIG. 4 in which IC's 140, 150, 160, 170 and 180 are mounted on the top surface 104 of substrate 102. Integrated circuits 145, 155, 165, 175, and 185 are encapsulated in cavities 142, 152, 162, 172 and 182, respectively, underneath IC's 140, 150, 160, 170, and 180. Thus, printed circuit board 100 includes 10 IC's—5 IC's mounted on the top surface 104 of substrate 102 and 5 more IC's mounted in cavities within substrate 102. Previous printed circuit board technology would have required enough surface area to mount all 10 IC's on the top surface 104 of the printed circuit board requiring a larger board.

Figure 1:
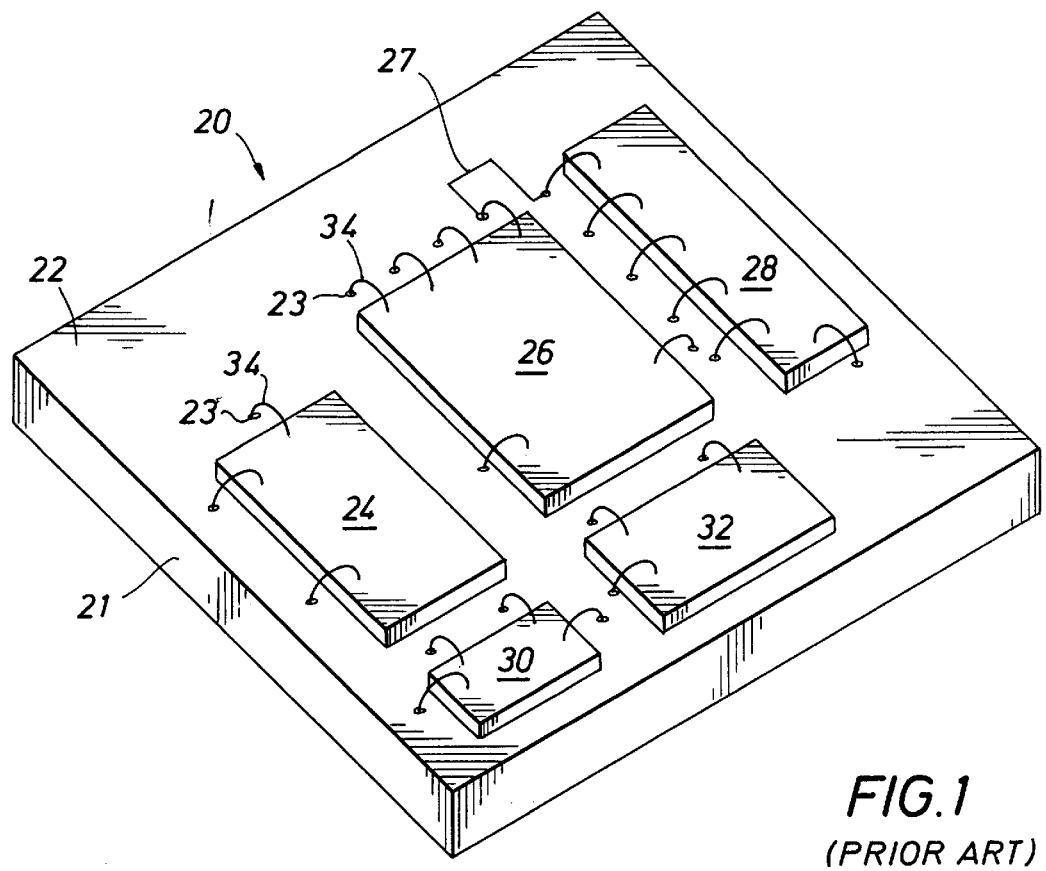
FIG. 1 shows a prior art printed circuit board including integrated circuits wire bonded to the top surface of the board.
Figure 2:
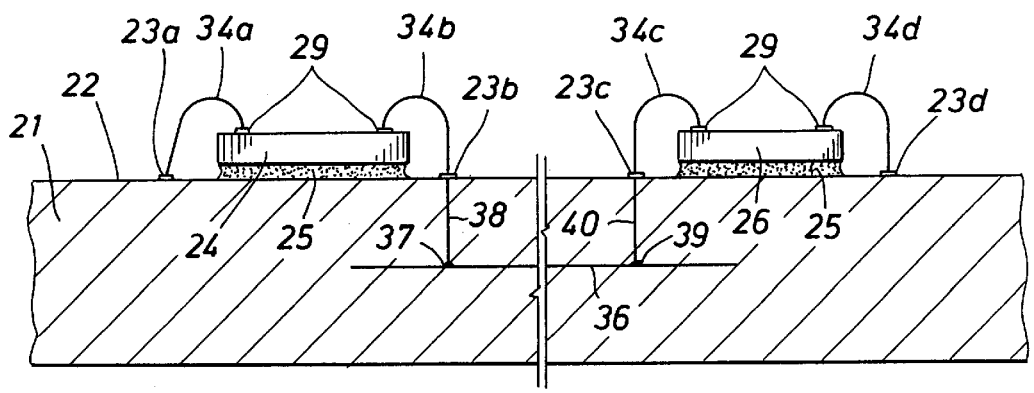
FIG. 2 shows a cross-sectional view of a prior art mounting technique for mounting integrated circuits on a printed circuit board.

Referring again to FIG. 3, encapsulating IC 114 in cavity 110 also allows for lower impedance electrical connections between IC 114 and IC 130. Lower impedance connections result from shorter conductive pathways between IC 114 and IC 130 because IC 130 is mounted directly over IC 114. Consequently, the conductive pathway between IC 114 and IC 130 comprising conductive channel 122, layer 126, conductive channel 124, and wire bond 134 is a shorter pathway than pathways in previous printed circuit board mounting arrangements, such as that shown in FIG. 2, in which the two connected IC's generally are mounted farther apart than in the preferred embodiment of FIG. 3. Accordingly, those electrical components whose interconnections preferably should have as low impedance as possible are mounted using the arrangement shown in FIG. 3.

It should be recognized that the dimensions of each cavity 110 should be slightly larger than the IC encapsulated within the cavity. Referring still to FIG. 3, the distance W between IC 114 and the side walls 117 of the cavity 110 is just enough to allow the encapsulation material (which initially is a liquid) 120 to flow down the sides of IC 114 and fill the space between the bottom of IC 114 and the bottom surface 118 of the cavity 110. Allowing the encapsulation material 120 to flow around the sides of IC 114 and underneath IC 114 allows the IC to be fully encapsulated and provides a reliable mounting arrangement. A distance W of 0.005"–0.010" along each side of IC 114 is generally believed to be sufficient for this purpose.

The depth D of cavity 110 should be greater than the combined height of the IC and the solder joints 116, as will be appreciated by one of ordinary skill in the art. The depth D preferably is large enough to allow encapsulation material to cover IC 114 when the IC is mounted in cavity 110, thereby providing a reliable, substantially planar surface 105 on which to mount IC 130. It is believed that the depth D of cavity 110 generally will be between 0.012" and 0.020" but the exact depth of a particular cavity will depend on the height of the IC encapsulated in the cavity. The thickness of a 10 layer printed circuit board substrate, which is typical in implantable devices, is generally between 0.050" and 0.060". Thus, the depth D of the cavity 100 preferably is less than one-half of the thickness of the substrate 102.

Figure 5:
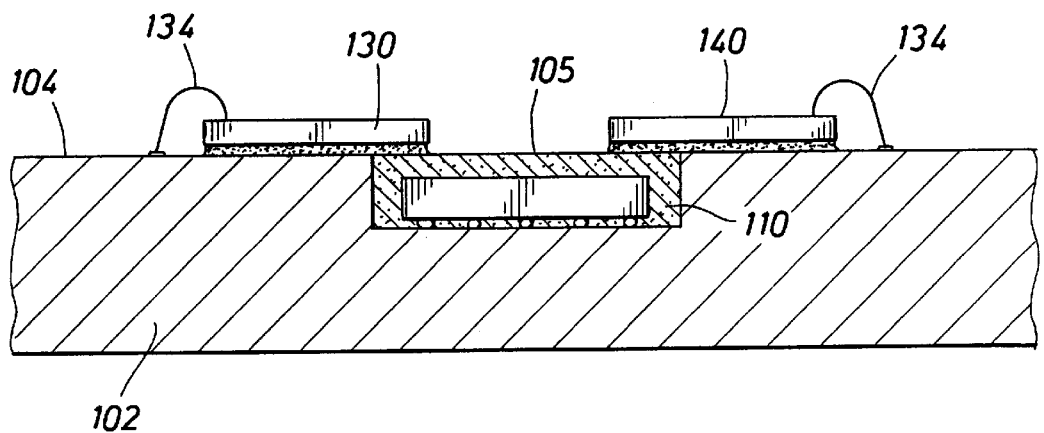
FIG. 5 shows a variation of the printed circuit board substrate and cavity arrangement of FIG. 3 in which two integrated circuits partially overlap an encapsulated device.

It should be recognized that integrated circuits or other electrical components mounted over an encapsulated IC may only partially overlap the footprint of the encapsulated IC. Referring to FIG. 5, for example, only a portion of IC's 130 and 140 overlap the footprint 105 of encapsulated IC 114.

Figure 6:
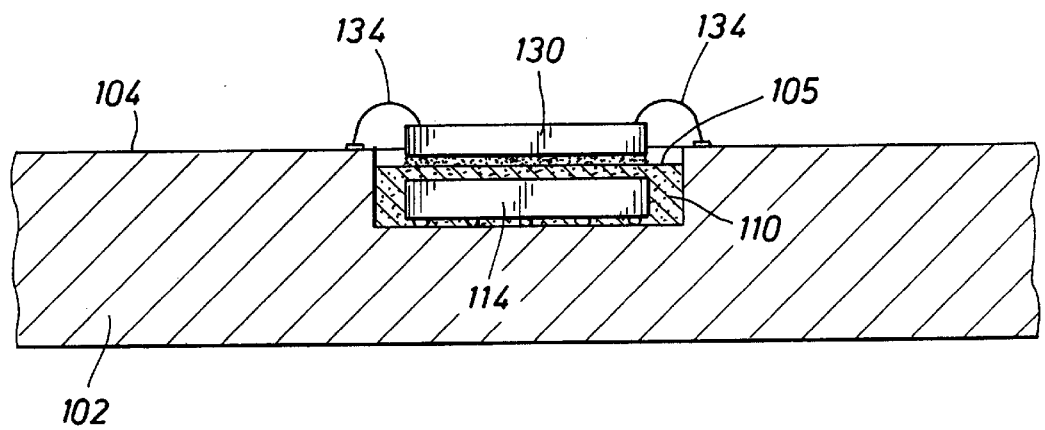
FIG. 6 is another variation of the substrate and cavity arrangement of FIG. 3 in which the top surface of the encapsulating material is below the top surface of the printed circuit board substrate.

The flip chip mounting configuration of FIG. 3 is preferred because it allows for the cavities to be as small as possible, both in the depth and width dimensions. Alternative embodiments to the flip chip mounting configuration of FIG. 3 are shown in FIGS. 6–9. Referring first to FIG. 6, it may be desired for the top surface of the encapsulating material to be below the top surface 104 of the PCB, rather than flush as shown in FIG. 3. As shown, IC 130 can be mounted on the footprint 105 of encapsulated IC 114, thereby reducing the overall thickness of the PCB.

Figure 7:
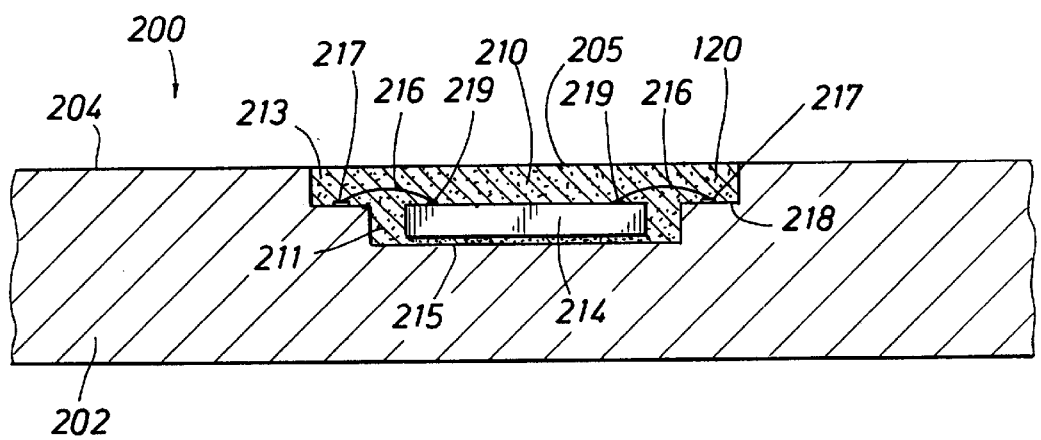
FIG. 7 is an alternative embodiment of the cavity arrangement of FIG. 3.

Referring now to FIG. 7, printed circuit board 200 includes a cavity 210 within substrate 202. The cavity 210 includes a lower portion 211 which is just large enough to encapsulate IC 214, and an upper portion 213. As shown, upper potion 213 is wider than lower portion 211 and the cavity includes a horizontal surface or ledge 218 between the upper portion 213 and lower portion 211. The IC 214 is mounted in the lower portion 211 by way of an adhesive 215, and wire bonds 216 electrically connect contacts 219 on the top surface of IC 214 to pads 217 on horizontal surfaces 218 between the upper portion 213 and the lower portion 211. The depth and width of the upper portion 213 should be large enough to accommodate the upward and outward bend of wire bonds 216. The IC 214 also is encapsulated in cavity 210 byway of encapsulation material 120, thereby providing a surface 205 contiguous with the top surface 204 of the substrate 202. Although not shown in FIGS. 7–9, other IC's can be mounted on the top surface of the substrate over the cavity as in FIGS. 3–6.

Figure 8:
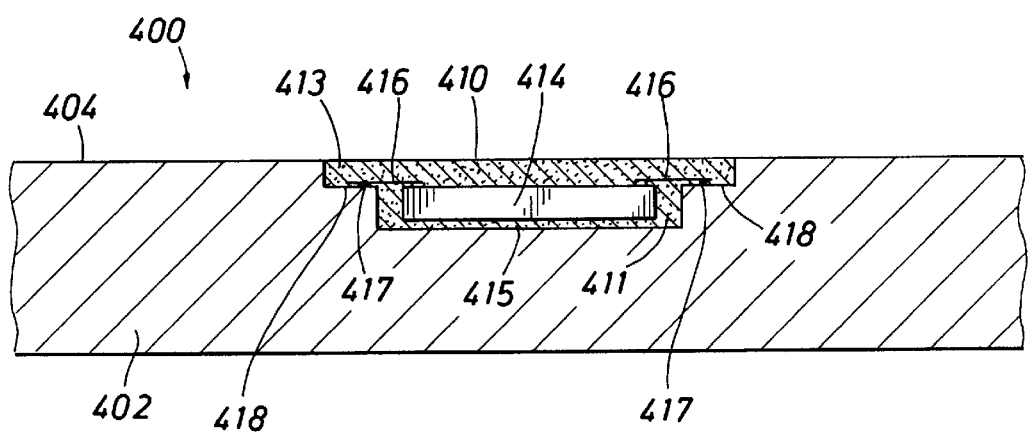
FIG. 8 is another alternative embodiment of the cavity arrangement of FIG. 3.

Alternatively and with reference to FIG. 8, an IC 414 can be mounted in a cavity 410 in a configuration similar to that of FIG. 7. Cavity 410 includes an upper portion 413 that, as in FIG. 5, is wider than a lower portion 411 in which IC 414 is mounted. A ledge 418 separates the lower portion 411 from the upper portion 413. Instead of wire bonds, however, conductive ribbons or tabs 416 are used to couple contacts on the IC 414 to pads 417 on the bottom surface 418 of cavity 410. An adhesive 415 bonds the IC 414 to the bottom surface 418 of the cavity 410. Because the tabs 416 lie flat, rather than looping up as for the wire bonds of FIG. 7, the cavity 410 can be shallower than cavity 210 in FIG. 7.

Figure 9:
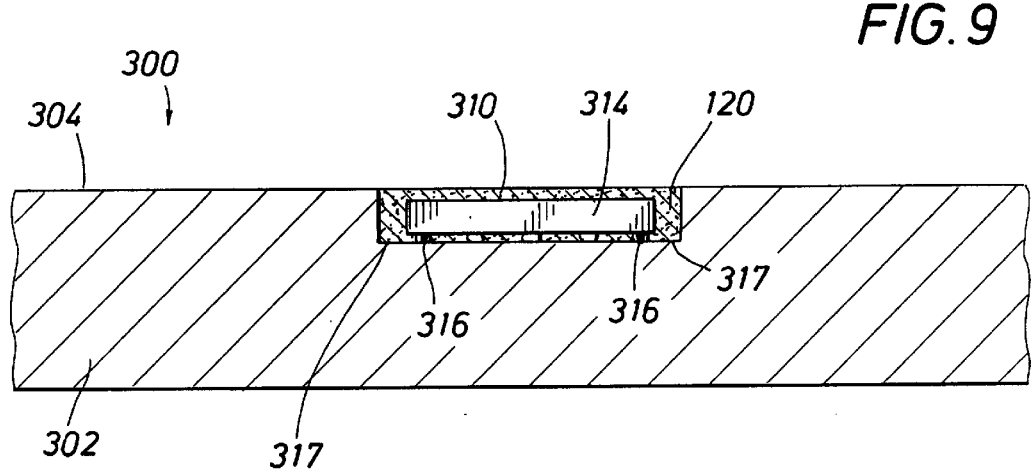
FIG. 9 is still another alternative embodiment of the cavity arrangement of FIG. 3.

Another alternative embodiment to the mounting configuration of FIG. 3 is shown in FIG. 9. A substrate 304 includes a cavity 310 in which an integrated circuit 314 is encapsulated with encapsulation material 120. The IC 314 is mounted in the cavity 310 in a "flip tab" configuration in which conductive tabs 316 electrically couple the IC 314 to pads 317 on the bottom surface of the cavity 310. A flip tab configuration is implemented by "flipping" over an IC with tab connections, such as IC 414 in FIG. 8. The flip tab configuration of FIG. 9, however, does not require a wider upper cavity portion as in FIGS. 7 and 8.

The depth and width dimensions of cavity 210 (FIG. 7), cavity 410 (FIG. 8), and cavity 310 (FIG. 9) are greater than cavity 110 in FIG. 3. However, such alternative embodiments may be necessary depending on the availability of IC package types. For example, the embodiment of FIG. 9 may be necessary if it is desired to encapsulate an IC that is only available in a flip tab configuration.

It is generally recognized that many functions of a circuit board cannot be tested until the circuit board is fully assembled and all the integrated circuits are mounted on the board. Testing of a fully assembled circuit board may reveal that one or more of the components are defective and must be replaced. Replacement, however of an integrated circuit that is encapsulated according to the preferred embodiments described above may be very difficult and expensive and may even require that the entire circuit board be scrapped. By contrast, integrated circuits mounted on the top surface of a substrate are much more easily replaced than encapsulated IC's. Thus, it may be desired that only the most reliable types of IC's, such as memory devices, be encapsulated according to the preferred embodiments. Memory IC's are generally regarded as very reliable technology and the risk of having a defective memory chip is sufficiently low to warrant encapsulating such a device. Further, it may be desired to encapsulate certain components when low impedance electrical connections, such as the connections between a battery charger circuit and a battery, are important.

Figure 10:
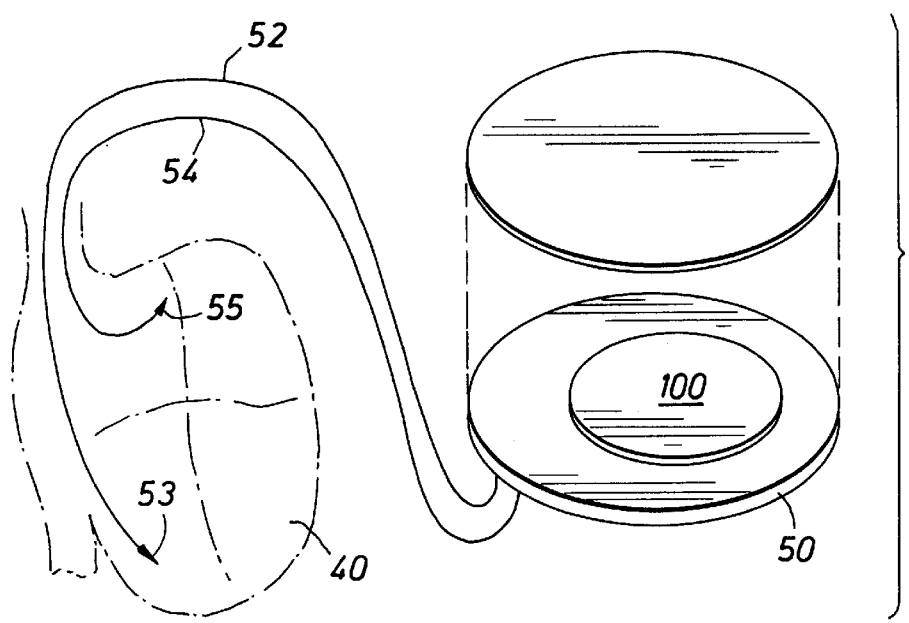
FIG. 10 shows a printed circuit board in accordance with a preferred embodiment of the invention mounted in an implantable pacemaker and coupled to a heart via leads and electrodes.

Referring now to FIG. 10, the printed circuit board 100 in accordance with a preferred embodiment of the invention is shown mounted in an implantable medical device 50, may be a pacemaker, defibrillator or other implantable device. The implantable device 50 couples to the heart 40 via leads 52 and 54. An electrode is attached to the distal end of each lead and is inserted into a chamber of the heart. Electrode 53 is attached to lead 52 and electrode 55 is attached to lead 54. It should be recognized that pacemaker 50 includes other components, such as a battery, that are not shown in FIG. 10. A multi-layer printed circuit board 100 included encapsulated electronic components advantageously allows an implantable medical device to include more components and further decrease the impedance of various electrical connections as compared to prior devices.

While preferred embodiments of this invention have been shown and described, modifications thereof can be made by one skilled in the art without departing from the spirit or teaching of this invention. The embodiments described herein are exemplary only and are not limiting. Many variations and modifications of the system and apparatus are possible and are within the scope of the invention. For example, it is intended that the invention include any technique for encapsulating an integrated circuit in a cavity within a substrate. A few such techniques have been described with reference to FIGS. 3, 5–9, but other configurations also are possible. Accordingly, the scope of protection is not limited to the embodiments described herein, but is only limited by the claims which follow, the scope of which shall include all equivalents of the subject matter of the claims.

What is claimed is:

1. A printed circuit board, comprising:
    a substrate including a top surface and a cavity;
    a first electronic device disposed in said cavity;
    encapsulation material covering said first electronic device and forming a support surface; and
    a second electronic device at least partially supported by said support surface of said encapsulating material,
    wherein said support surface has a first predetermined surface area and said second electronic device has a footprint of a second predetermined area, and wherein said second predetermined area is less than said first predetermined area.

2. The printed circuit board of claim 1 wherein said support surface of said encapsulating material is substantially coplanar with said top surface of said substrate.

3. The printed circuit board of claim 1 wherein said first electronic device is an integrated circuit.

4. The printed circuit board of claim 3 said second electronic device is an integrated circuit.

5. The printed circuit board of claim 1 wherein said second electronic device is mounted on said substrate such that said footprint is entirely within said first predetermined surface area.

6. A printed circuit board, comprising:
    a substrate including a top surface and a cavity:
    a first electronic device disposed in said cavity;
    encapsulation material covering said first electronic device and forming a support surface; and
    a second electronic device at least partially supported by said support surface of said encapsulating material,
    wherein said support surface of said encapsulating material is recessed from said top surface of said substrate.

7. An implantable medical device comprising:
    an electrode configurable to deliver an electrical shock to a heart; and
    a printed circuit board configured to provide said electrical shock, wherein the printed circuit board comprises:
        a substrate including a top surface and a cavity;
        a first electronic device mounted in said cavity;
        encapsulation material covering said first electronic device and forming a support surface; and
        a second electronic device at least partially supported by said support surface of said encapsulating material,
        wherein said support surface has a first predetermined surface area and said second electronic device has a footprint of a second predetermined area, and wherein said second predetermined area is less than said first predetermined area.

8. An implantable medical device which comprises:
    an electrode configurable to deliver an electrical shock to a heart; and
    a printed circuit board configured to provide said electrical shock, wherein the printed circuit board comprises:
        a substrate including a top surface and a cavity;
        a first electronic device mounted in said cavity;
        encapsulation material covering said first electronic device and forming a support surface; and
        a second electronic device at least partially supported by said support surface of said encapsulating material,
        wherein said support surface of said encapsulating material is recessed from said top surface of said substrate.

* * * * *